US009020576B2

(12) United States Patent
Nagatani (10) Patent No.: US 9,020,576 B2
(45) Date of Patent: Apr. 28, 2015

(54) BIOLOGICAL MEASUREMENT APPARATUS AND BIOLOGICAL STIMULATION APPARATUS

(75) Inventor: Yukinori Nagatani, Okazaki (JP)

(73) Assignee: Okayama Prefecture, Okayama (JP)

(*) Notice: Subject to any disclaimer, the term of this patent is extended or adjusted under 35 U.S.C. 154(b) by 697 days.

(21) Appl. No.: 12/935,279

(22) PCT Filed: Mar. 31, 2008

(86) PCT No.: PCT/JP2008/056304
§ 371 (c)(1),
(2), (4) Date: Sep. 28, 2010

(87) PCT Pub. No.: WO2009/122485
PCT Pub. Date: Oct. 8, 2009

(65) Prior Publication Data
US 2011/0054345 A1 Mar. 3, 2011

(51) Int. Cl.
*A61B 5/05* (2006.01)
*A61B 5/00* (2006.01)
(Continued)

(52) U.S. Cl.
CPC .............. *A61B 5/05* (2013.01); *A61B 5/04001* (2013.01); *A61B 5/0051* (2013.01); *A61B 5/055* (2013.01); *A61N 5/00* (2013.01)

(58) Field of Classification Search
CPC .... A61B 5/0051; A61B 5/04; A61B 5/04001; A61B 5/04004; A61B 5/055
USPC .................................. 600/544, 13, 310, 552
See application file for complete search history.

(56) References Cited

U.S. PATENT DOCUMENTS

| 5,738,625 A | 4/1998 | Gluck |
| 5,752,515 A | 5/1998 | Jolesz et al. |
| 6,016,449 A * | 1/2000 | Fischell et al. ............... 607/45 |

(Continued)

FOREIGN PATENT DOCUMENTS

| JP | 07-143971 A | 6/1995 |
| JP | 8-140954 A | 6/1996 |

(Continued)

OTHER PUBLICATIONS

International Search Report received for PCT Patent Application No. PCT/JP2008/056304, mailed on May 13, 2008, 3 pages of International Search Report and 4 pages of English Translation.

(Continued)

*Primary Examiner* — Max Hindenburg
*Assistant Examiner* — John Pani
(74) *Attorney, Agent, or Firm* — Morrison & Foerster LLP (57) ABSTRACT

A biological measurement apparatus of this invention includes (i) a micro piezoelectric element for vibrating a nerve cell of a subject without coming in contact with the nerve cell, (ii) an electromagnetic wave antenna for receiving an electromagnetic wave generated by the nerve cell vibrated by the micro piezoelectric element, and (iii) a computer for measuring an electric charge of the nerve cell based on the electromagnetic wave received by the electromagnetic wave antenna. Further, this biological measurement apparatus includes an electromagnetic wave antenna for emitting an electromagnetic wave to a nerve cell. This configuration provides an apparatus capable of measuring an electrical activity of a nerve cell in a living organism in real time and three-dimensionally at a spatial resolution of a nerve cell size. Moreover, this configuration provides an apparatus capable of individually giving electrical stimulations to any desired cells in the subject.

9 Claims, 3 Drawing Sheets

(51) Int. Cl.
*A61B 5/04* (2006.01)
*A61B 5/055* (2006.01)
*A61N 5/00* (2006.01)

(56) References Cited

U.S. PATENT DOCUMENTS

| | | | |
|---|---|---|---|
| 2001/0027336 A1* | 10/2001 | Gielen et al. | 607/116 |
| 2004/0122323 A1 | 6/2004 | Vortman et al. | |
| 2007/0135755 A1* | 6/2007 | Bernabei | 604/20 |
| 2008/0140149 A1* | 6/2008 | John et al. | 607/45 |
| 2008/0208287 A1* | 8/2008 | Palermo et al. | 607/48 |
| 2009/0221900 A1* | 9/2009 | Ikushima et al. | 600/409 |

FOREIGN PATENT DOCUMENTS

| | | |
|---|---|---|
| JP | 2006-511265 A | 4/2006 |
| JP | 2007-195779 A | 8/2007 |
| JP | 2008-093286 A | 4/2008 |
| WO | 2006/044793 A2 | 4/2006 |

OTHER PUBLICATIONS

Office Action received for Japanese Patent Application No. 2006-280558, mailed on Mar. 13, 2012, 5 pages (3 pages of English translation and 2 pages of Office Action).

* cited by examiner

BIOLOGICAL MEASUREMENT APPARATUS AND BIOLOGICAL STIMULATION APPARATUS

CROSS REFERENCE TO RELATED APPLICATIONS

This is a U.S. National Phase patent application of PCT/JP2008/056304, filed Mar. 31, 2008, which is hereby incorporated by reference in the present disclosure in its entirety.

TECHNICAL FIELD

The present invention relates to a biological measurement apparatus and a biological stimulation apparatus. More specifically, the present invention relates to (i) a biological measurement apparatus for measuring an electrical activity of the brain or the like of a subject in such a manner that the biological measurement apparatus (a) vibrates a nerve cell of the subject so that an electromagnetic wave is generated and (b) detects the electromagnetic wave, and (ii) a biological stimulation apparatus for giving an electrical stimulation to a nerve cell of a subject in such a manner that the biological stimulation apparatus (a) emits an electromagnetic wave to the nerve cell so that an oscillating magnetic field is formed around the nerve cell and (b) vibrates the nerve cell so that an electromotive force is generated in the nerve cell.

BACKGROUND ART

Researches on diseases and disorders related to the brain and nerves are now vigorously carried out. In order to diagnose and treat the diseases and disorders related to the brain and nerves, it is important to measure electrical activities of nerve cells in the brain or the like and to arbitrarily stimulate individual nerve cells.

Synaptic transmission between nerve cells is carried out by (i) direct transmission of an electric signal between the nerve cells or (ii) transfer of an electric charge between the nerve cells, which transfer is mediated by an ionic chemical substance such as $Ca^{2+}$. In either case, the synaptic transmission takes place by a change in an electric charge of the inside and the cell wall, etc. of each individual cell. Thus, for ease of explanation, the term "electrical activity" herein encompasses transmission of an electric signal, transmission of an action potential, and a change in an electric charge of each individual nerve cell.

Conventionally, the below-described techniques have been conducted for (i) measurement of the brain and (ii) stimulation of a nerve cell:

The X-ray CT scanning (X-ray computed tomography) is a technique carried out as follows: X-rays are emitted to a living subject, and three-dimensional distribution of an amount of X-rays absorbed by the living body is measured with a high resolution.

The magnetic resonance imaging (MRI) is a technique that utilizes nuclear magnetic resonance (NMR) of, e.g., a hydrogen atom in a magnetic field. Namely, the MRI emits, in a strong magnetic field with gradient, an electromagnetic wave to a living subject, detects an electromagnetic wave emitted by the living subject in response to the emission, and three-dimensionally visualizes the state of the hydrogen atoms with use of a computer or the like. In particular, the functional MRI (fMRI) can three-dimensionally detect the phenomenon that oxyhemoglobin in the blood is converted into deoxyhemoglobin. Based on the result, the fMRI can specify an activated region in the brain in which region oxygen is being consumed.

The positron emission tomography (PET) and the single photon emission computed tomography (SPECT) are techniques carried out as follows: Substances (radioactive tracers) each labeled with a radioisotope are administered to a living subject, gamma rays emitted by the radioactive tracers are detected with use of gamma-ray detectors arranged around the living subject, and three-dimensional distribution of the radioactive tracers in the living body is measured with use of a computer or the like. Particularly, if FDG (18F Fluoro Deoxy Glucose), which is a glucose labeled with a radioisotope, is used as the radioactive tracer (FDG-PET), it is possible to visualize the activity of the brain by three-dimensionally measuring distribution of glucose metabolism.

The magnetoencephalography (MEG) is a technique carried out as follows: A number of high-sensitive magnetic sensors such as superconduction quantum interference devices (SQUIDs) are arranged around the head of a subject, and fluctuations in magnetic fields caused by electrical activities of nerve cells are measured therewith. Thus, the MEG can directly observe the electrical activities of the nerve cells. Further, the MEG has a big advantage of being capable of carrying out measurement nondestructively and noninvasively.

The electroencephalography (EEG) includes (i) the scalp EEG, which is noninvasive, and (ii) the electrocorticogram, which is invasive. The scalp EEG is a technique for detecting, with use of a number of electrodes set on the scalp of a subject, changes in an electric potential leaked via the dura mater, the cranial bone, and the scalp, so as to measure an electrical activity of the brain of the subject. Thus, the scalp EEG is simple and noninvasive. The electrocorticogram is a technique for inserting electrodes into the surface and the inside of the brain through craniotomy operation so as to directly measure an electrical activity of the brain.

The optical topography (OT) and the near-infrared spectroscopy (NIRS) are techniques both utilizing the characteristics of near-infrared light that the near-infrared light is easy to diffuse and transmit through a living subject. Namely, each of these techniques uses near-infrared light to observe changes in an oxyhemoglobin-to-deoxyhemoglobin ratio in the brain of a subject, which changes are caused by nervous activity. Specifically, each of these techniques is carried out in the following manner: A plurality of optical elements are set around the head of the subject, near-infrared rays of different wavelengths are emitted to the head, and light reflected by the head is detected. Thus, these techniques are completely noninvasive.

The ultrasonography is a technique carried out as follows: A sound wave is emitted to a living subject, the sound wave reflected by the living subject is detected, and three-dimensional distribution of acoustic impedance in the living subject is measured. The ultrasonography is nondestructive and noninvasive, and has a big advantage of being easy to carry out. Further, by using a sound wave having a shorter wavelength, it is possible to improve the spatial resolution.

Meanwhile, as a technique for giving an electrical stimulation to a nerve cell, the following techniques have been proposed: (i) A technique for inserting an electrode needle into a subject so as to directly give an electrical stimulation to the subject. (ii) Magnetic pulse stimulation (transcranial magnetic stimulation; TMS) that utilizes the principle of electromagnetic induction to directly give an electrical stimulation to a subject by an electromotive force.

The above-mentioned techniques for measurement with respect to a living body (e.g., the brain) are comprehensively explained in Non-Patent Literature 1, for example.

Non-Patent Literature 1

Tsunehiro Takeda, "Nou Kougaku (Brain Engineering)", Corona Publishing, Co., Ltd., Edited by the Institute of Electronics, Information and Communication Engineers, Apr. 11, 2003

SUMMARY OF INVENTION

The above-described techniques for measurement of the brain, however, involve the problem of being incapable of measuring the electrical activity in real time at a spatial resolution of a nerve cell size.

In the X-ray CT scanning, the absorption amount of X-ray does not reflect transmission of an electrical activity between the nerve cells. Therefore, according to the principle of the X-ray CT scanning, it is impossible to measure the electrical activity. Furthermore, the X-ray CT scanning also involves the problem of exposing the subject to X-rays.

According to the principle of the fMRI, a limit spatial resolution of the fMRI is a size of the blood capillary in the brain. Technically, the limit spatial resolution of the fMRI is in the sub-millimeter range. Therefore, with the fMRI, it is impossible to directly measure electrical activities of individual nerve cells. Furthermore, with the fMRI, the measurement must be carried out in a strong magnetic field. Therefore, the fMRI requires a huge magnet, and thus needs expensive equipment.

In the PET, a distance in the millimeter range is necessary between discharge of a positron and annihilation of the positron. Thus, the point at which the positron is discharged, i.e., the point at which the radioactive tracer is located, is different from the point at which the positron is annihilated and emits a gamma ray. Thus, according to the principle of the PET, a limit spatial resolution of the PET is in the millimeter range. Meanwhile, the SPECT has a limitation on its angular resolution for gamma rays; therefore, its resolution cannot exceed that of the PET. Furthermore, the PET and the SPECT, both of which utilize a radioisotope, involve the problem of exposure to radiation. In addition, the PET and the SPECT each require a huge, expensive particle accelerator (e.g., a cyclotron) as a device for producing a radioisotope having a short half-life.

The EEG measures the electrical activity three-dimensionally by using differences in time taken for fluctuated magnetic fields to reach the EEG. However, since the time scale of the fluctuations in the magnetic fields is as long as a few milliseconds, an electromagnetic wave to be used has a very long wavelength. Consequently, the MEG has a rough spatial resolution (i.e., in the submillimeter range), and therefore cannot measure electrical activities of individual nerve cells.

The scalp EEG has a poor spatial resolution, and therefore can measure only an average of electrical activities of a number of nerve cells. The electrocorticogram, which needs a large-scale craniotomy operation, is highly invasive for a subject. Therefore, the electrocorticogram is difficult to apply to three-dimensional measurement of the entire brain.

The OT and the NIRS each carry out the measurement by using diffused light; therefore, they cannot carry out the measurement by converging light to a single point. Thus, each of the OT and the NIRS has a spatial resolution in the centimeter range, and therefore cannot detect the electrical activity.

In the ultrasonography, the acoustic impedance reflects a density and hardness of a nerve cell, but does not reflect the electrical activity. Therefore, according to the principle of the ultrasonography, it is impossible to measure the electrical activity.

Meanwhile, the above-described conventional techniques for stimulating a nerve cell involve the problems of high invasiveness for a subject and a poor spatial resolution.

Specifically, the technique for inserting an electrode needle into a subject so as to give an electrical stimulation to the subject is highly invasive for the subject. Furthermore, it is substantially impossible to give electrical stimulations to the subject at many points in a broad range.

In the magnetic pulse stimulation, an applicable electromagnetic wave has a wavelength which is far larger than a nerve cell size. Thus, the magnetic pulse stimulation has a poor spatial resolution, and therefore cannot give electrical stimulations to individual nerve cells.

The present invention was made in view of the foregoing problems, and an object of the present invention is to provide a device for three-dimensionally and in real time measuring an electrical activity of a nerve cell in a living subject at a spatial resolution of a nerve cell size. Another object of the present invention is to provide a device for individually giving electrical stimulations to any nerve cells of a subject.

In order to attain these objects, the present inventors conducted diligent studies. As a result, the present inventors found that mechanically vibrating a nerve cell having an electric charge results in generation of an electromagnetic wave, as a result of bremsstrahlung according to the Maxwell's equations of electromagnetism, which occurs due to the vibration and an oscillating current generated by the vibration. Based on this, the present inventors reached the present invention which can carry out, by detecting the electromagnetic wave thus generated, high-sensitive measurement of an electrical activity of the nerve cell without coming in contact with the nerve cell and being interfered by bones and/or the like of the subject. In addition, the present inventors also found that emission of an electromagnetic wave to a nerve cell artificially generates an oscillating magnetic field around the nerve cell, and mechanically vibrating the nerve cell at the time results in generation of an electromotive force in the nerve cell. Based on this, the present inventors reached the present invention which is capable of giving an electrical stimulation to a nerve cell without coming in contact with the nerve cell.

Namely, in order to attain the foregoing objects, a biological measurement apparatus of the present invention includes: one or more vibrating elements each for vibrating a nerve cell of a subject without coming in contact with the nerve cell; an electromagnetic wave receiving element for receiving an electromagnetic wave generated by the nerve cell which is vibrated by the vibrating element; and an analyzing means for analyzing an amount and a sign of an electric charge of the nerve cell based on the electromagnetic wave received by the electromagnetic wave receiving element.

According to this configuration, it is possible to vibrate a nerve cell without coming in contact with the nerve cell. Since the nerve cell has an electric charge, vibrating the nerve cell results in generation of an oscillating current. Due to the oscillating current, an electromagnetic wave is generated according to the Maxwell's equations. Then, the electromagnetic wave thus generated is received and converted into numerical data, which is then analyzed by, e.g., the three-dimensional Radon transform. Thus, it is possible to obtain three-dimensional electric charge distribution in nerve cells in the subject. Further, with this configuration, after the nerve cell is vibrated, an electromagnetic wave generated in response to the vibration is received within a quite short time. Therefore, it is possible to measure the electric charge distribution in the subject in real time. Furthermore, this configuration is free from exposure to radiation, which is the problem of the X-ray CT scanning. Moreover, this configuration does not need a huge magnet, which is necessary for the MRI. Thus, with this configuration, it is possible to grasp an electric activity in the subject more safely than the X-ray CT scanning and more easily than the MRI.

Hence, with this configuration, it is possible to safely, easily, three-dimensionally, and in real-time grasp (i) electric charge distribution of a nerve cell in a subject, consequently (ii) an electric activity in the subject.

In the biological measurement apparatus of the present invention, it is preferable that the vibrating element emits a sound wave so as to vibrate the nerve cell.

With this configuration, it is possible to vibrate the nerve cell by the sound wave. Since the sound wave is easy to generate, this configuration makes it possible to more easily carry out the measurement of the electric charge of the nerve cell.

In the biological measurement apparatus of the present invention, it is preferable that the sound wave has a vibration frequency of 1 MHz or more and not more than 1 GHz.

With this configuration, it is possible to improve the temporal resolution, since the vibration frequency of 1 MHz or more and not more than 1 GHz is sufficiently larger than the time scale (approximately 100 Hz) of an electrical activity of a nerve cell. Furthermore, the sound wave having the vibration frequency of 1 MHz or more and not more than 1 GHz has a wavelength which is almost equal to a length of the nerve cell. Thus, it is possible to provide a biological measurement apparatus having a spatial resolution of a nerve cell size level.

In the biological measurement apparatus of the present invention, it is preferable that the vibrating element has a region whose area is 1 $\mu m^2$ or more and not more than 1 $mm^2$, from which region the sound wave is emitted.

With this configuration, it is possible to vibrate individual nerve cells. Thus, it is possible to provide a biological measurement apparatus having a spatial resolution of a nerve cell size level.

The biological measurement apparatus of the present invention preferably includes a plurality of vibrating means units each provided with a vibrating element array in which the vibrating elements are arranged two-dimensionally.

According to this configuration, it is possible to manufacture the biological measurement apparatus in such a manner that a plurality of vibrating element arrays are prepared as respective units in advance and then these units are combined together. Thus, it is possible to manufacture the biological measurement system easily.

In the biological measurement apparatus of the present invention, it is preferable that the vibrating element is provided on a surface of a substrate which surface faces the subject, the substrate covering at least part of a surface of the subject.

With this configuration, it is possible to externally vibrate a nerve cell in the subject. Thus, it is possible to measure an electric charge of the nerve cell in a manner noninvasive for the subject.

In the biological measurement apparatus of the present invention, it is preferable that the substrate covers at least part of a surface of a head of the subject.

According to this configuration, the substrate covers the head. Therefore, it is possible to easily vibrate a nerve cell in the brain. Thus, it is possible to more easily and noninvasively measure an electric charge of the nerve cell in the brain of the subject.

In the biological measurement apparatus of the present invention, it is preferable that the vibrating element is provided on a surface of a substrate which has a plate-like shape and is to be inserted into the inside of the subject.

With this configuration, it is possible to vibrate a nerve cell without being affected by, e.g., the cranium of the subject. Thus, it is possible to provide a biological measurement apparatus capable of detecting an electric charge of a nerve cell with a high sensitivity.

It is preferable that the biological measurement apparatus of the present invention further includes: an electromagnetic wave emitting element for emitting an electromagnetic wave to the nerve cell.

With this configuration, it is possible to emit an electromagnetic wave to a nerve cell for forming an oscillating magnetic field around the nerve cell, and to vibrate the nerve cell by the vibrating element. Consequently, an electromotive force is generated in the nerve cell according to the Fleming's law. Thus, it is possible to give an electrical stimulation to a nerve cell.

In the biological measurement apparatus of the present invention, it is preferable that at least one of the electromagnetic wave receiving element and the electromagnetic wave emitting element is provided in a vibrating means unit provided with a vibrating element array in which the vibrating elements are arranged two-dimensionally.

According to this configuration, in which at least one of the electromagnetic wave receiving element and the electromagnetic wave emitting element is provided in the vibrating means unit in advance, it is possible to simplify the manufacturing steps, since this configuration eliminates a need for providing the electromagnetic wave receiving element and the electromagnetic wave emitting element for each individual biological measurement apparatus. This makes it possible to provide a biological measurement apparatus at a low price.

In the biological measurement apparatus of the present invention, it is preferable that the electromagnetic wave receiving element and the electromagnetic wave emitting element are provided as a single antenna.

With this configuration, it is not necessary to manufacture the electromagnetic wave receiving element and the electromagnetic wave emitting element separately. This reduces the number of components necessary for the biological measurement apparatus. Thus, it is possible to provide a biological measurement apparatus at a lower price.

In the biological measurement apparatus of the present invention, it is preferable that, in a case where the biological measurement apparatus is used while being connected with an external device, based on the electromagnetic wave received, the analyzing means calculates a signal for driving the external device and supplies the signal to the external device, and based on information obtained by the external device, the analyzing means calculates a signal for driving the vibrating element and supplies the signal to the vibrating element.

With this configuration, an intention of a subject of the biological measurement apparatus can be reflected to operation for the external device via the biological measurement apparatus. Further, information from the external device can be directly transmitted to the brain of the subject. Thus, it is possible to operate the external device according to the subject's intention. In addition, the above configuration enables direct information exchange (interface) between the brain and a computer. With this, the brain and the computer can carry out information processing (e.g., calculations and/or thinking) in a manner as if the brain and the computer are integrated into one.

In the biological measurement apparatus of the present invention, it is preferable that the analyzing means analyzes a nervous system of the subject based on the electromagnetic wave received by the electromagnetic wave receiving element.

With this configuration, it is possible to study the nervous system of the subject by analyzing the nervous system based on the electromagnetic wave thus received. Thus, for example, it is possible to obtain information necessary for treatments for the Parkinson's disease or severe depression by studying the nervous system of a subject presenting with symptoms of these diseases.

In the biological measurement apparatus of the present invention, it is preferable that the analyzing means calculates (i) a requirement for an electrical stimulation to cause a nervous system having an abnormality to be normal and (ii) a requirement for a vibration and an electromagnetic wave to give the electrical stimulation to a nerve cell; and based on the requirement for the vibration and the electromagnetic wave, the analyzing means calculates a signal for driving the vibrating element and supplies the signal to the vibrating element, and the analyzing means calculates a signal for driving the electromagnetic wave emitting element and supplies the signal to the electromagnetic wave emitting element.

With this configuration, it is possible to give a nerve cell an electrical stimulation by which a nervous system having an abnormality becomes normal, thereby constructing a normal nervous system. For example, it is possible to treat the Parkinson's disease and severe depression by constructing a normal nervous system which is free from symptoms of these diseases.

In order to attain the foregoing objects, a biological stimulation apparatus of the present invention includes: one or more vibrating elements each for vibrating a nerve cell of a subject without coming in contact with the nerve cell; and an electromagnetic wave emitting element for emitting an electromagnetic wave to the nerve cell vibrated by the vibrating element.

With this configuration, it is possible to vibrate a nerve cell of a subject and to emit an electromagnetic wave to the nerve cell for formation of an oscillating magnetic field around the nerve cell. This results in generation of an electromotive force in the nerve cell, thereby making it possible to give an electrical stimulation to the nerve cell. That is, it is possible to give electrical stimulations to individual nerve cells noninvasively.

For a fuller understanding of the nature and advantages of the invention, reference should be made to the ensuing detailed description taken in conjunction with the accompanying drawings.

REFERENCE SIGNS LIST

1 Biological measurement apparatus
2 Sound sending/receiving unit assembly
3 Sound sending/receiving unit (vibrating means unit)
4 Micro piezoelectric element array (vibrating element array)
5 Sound wave sending/receiving circuit
6 Piezoelectric element driving circuit array
7 Sound wave detecting circuit array
8 Electromagnetic wave sending/receiving system
9 Electromagnetic wave antenna (electromagnetic wave receiving element, electromagnetic wave emitting element)
10 Electromagnetic wave sending/receiving circuit
11 Electromagnetic wave sending circuit
12 Electromagnetic wave receiving circuit
13 Computer (analyzing means)
15 Input/output device
17 Subject
18 Substrate
19 Micro piezoelectric element (vibrating element)
20 External device

DESCRIPTION OF EMBODIMENTS

The following will describe an embodiment of the present invention with reference to FIGS. 1 through 5. A biological measurement apparatus of the present embodiment is targeted at a human as a subject, and measures an electric charge of a nerve cell in the brain of the human or stimulates the nerve cell. However, the present invention is not limited to this.

[Configuration of Biological Measurement Apparatus]

Figure 1:
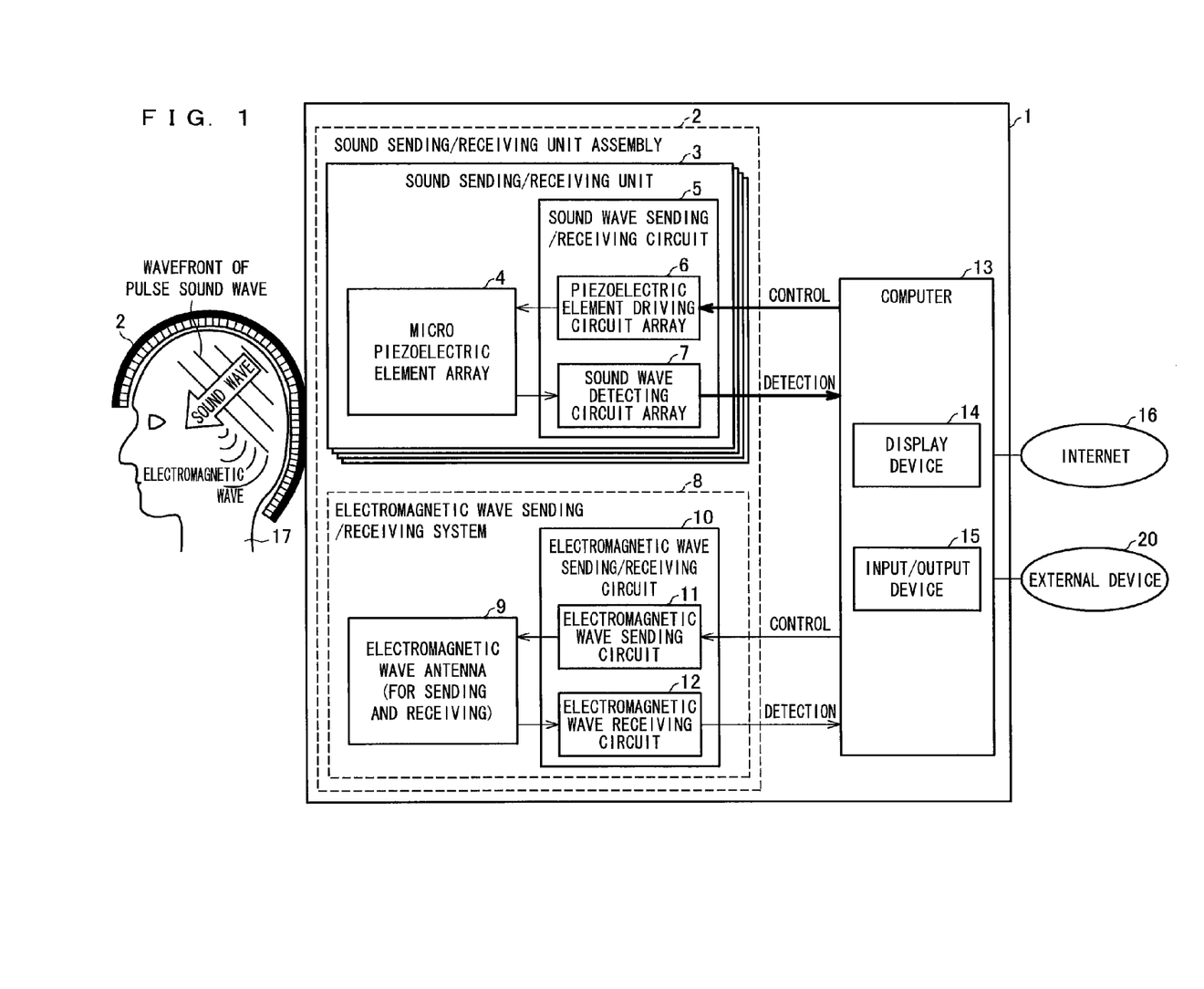
FIG. 1 is a view schematically illustrating a configuration of a biological measurement apparatus of one embodiment of the present invention.
Figure 2:
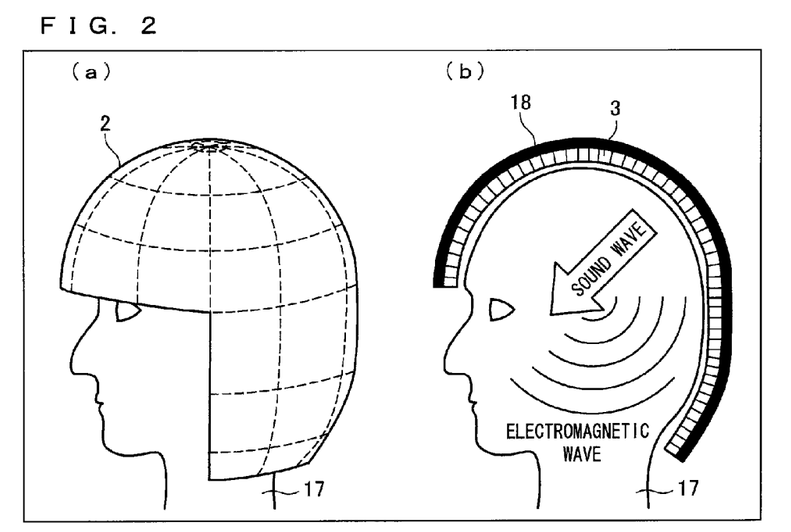
FIG. 2 is a view schematically illustrating an exterior outlook and a cross-sectional configuration of a sound sending/receiving unit assembly for use in the biological measurement apparatus of the one embodiment of the present invention. (a) of FIG. 2 shows the exterior outlook, and (b) of FIG. 2 shows the cross-section.
Figure 3:
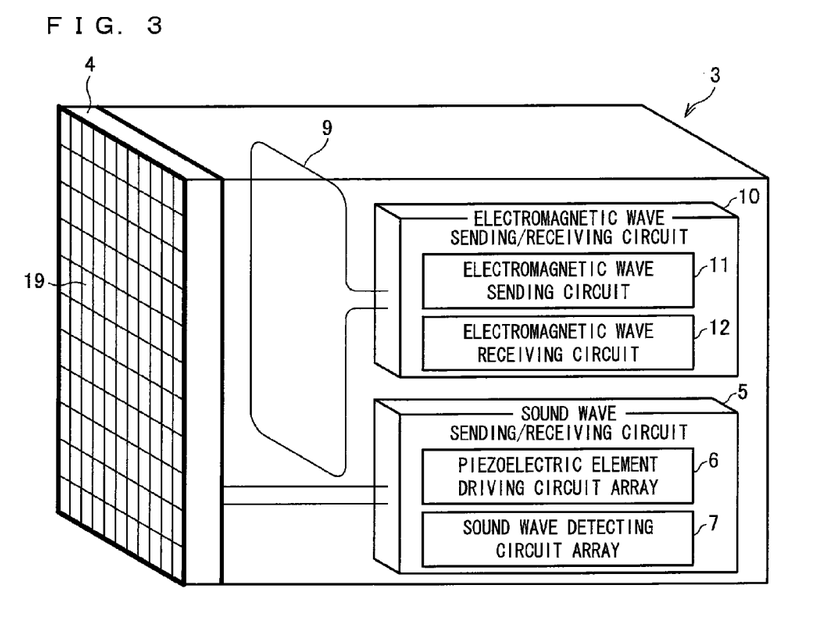
FIG. 3 is a view schematically illustrating a configuration of a sound sending/receiving unit for use in the biological measurement apparatus of the one embodiment of the present invention.

First, the following will explain a configuration of a biological measurement apparatus of the present invention with reference to FIGS. 1 through 3.

FIG. 1 is a view schematically illustrating a configuration of a biological measurement apparatus 1 of the present embodiment. FIG. 2 is a view schematically illustrating an exterior outlook and a cross-sectional configuration of a sound sending/receiving unit assembly 2 included in the biological measurement apparatus 1 of the present embodiment.

As shown in FIG. 1, the biological measurement apparatus 1 of the present embodiment includes the sound sending/receiving unit assembly 2 and a computer 13 (analyzing means). The computer 13 includes (i) a display device 14 for displaying data obtained as a result of measurement and (ii) an input/output device 15. The computer 13 is connected with the Internet 16 and an external device 20.

As shown in FIG. 2, the sound sending/receiving unit assembly 2 includes (i) a substrate 18 which covers the head of a subject 17 (ii) and a plurality of sound sending/receiving units (vibrating means units) 3. The sound sending/receiving units 3 are disposed on a surface of the substrate 18 facing the subject 17, in such a manner that the sound sending/receiving units 3 are close to each other.

The substrate 18 is preferably designed so as to surround (i) a region of a surface of the subject for which region measurement or stimulation is to be carried out and (ii) the vicinity of the region, and to come in close contact with the subject. For example, in a case where measurement or stimulation of a nerve cell in the brain is intended as in the present embodiment, the substrate 18 may have a hemispherical shape or a cylindrical shape. Preferably, however, the substrate 18 has a helmet-like shape, as shown in FIGS. 1 and 2. Further, a space between the sound sending/receiving unit assembly 2 and the surface of the subject is preferably filled with a liquid, for example, a lotion used in ultrasonographic examinations. This is because that such the configuration prevents unwanted reflection of a sound wave, thereby resulting in efficient and accurate propagation of the sound wave into the body.

If invasive examinations are permitted (e.g., when the subject 17 is an animal other than a human) or high accuracy and reliability are required for some reasons, the sound sending/receiving unit assembly 2 can be set to a position inner than the cranium of the subject through invasive operation or the like. This makes it possible to carry out measurement with an extremely high spatial resolution and to give an electrical stimulation to a nerve cell (described later). In such a case, the substrate included in the biological measurement apparatus of the present invention may have a plate-like shape, and may have a surface on which the sound sending/receiving unit assembly 2 is provided.

FIG. 3 is a view schematically illustrating a configuration of one of the sound sending/receiving units 3. The following will describe the sound sending/receiving unit 3 with reference to FIGS. 1 and 3.

The sound sending/receiving unit (vibrating means unit) 3 has a surface facing the subject and being provided with a corresponding micro piezoelectric element array 4 (vibrating element array) in which micro piezoelectric elements 19 (vibrating elements) are arranged two-dimensionally. The sound sending/receiving unit 3 also includes a sound wave sending/receiving circuit 5, which includes a piezoelectric element driving circuit array 6 and a sound wave detecting circuit array 7. The sound wave sending/receiving circuit 5 is electrically connected with the micro piezoelectric element array 4. The micro piezoelectric element arrays 4 are independently driven by their corresponding piezoelectric element driving circuit arrays 6.

The description in the present embodiment deals with a case where each of the micro piezoelectric elements 19 has an area of 100 $\mu m^2$. The area of each of the micro piezoelectric elements 19 may be optionally set depending on the desired measurement and/or spatial resolution for stimulation, and thus is not particularly limited. Preferably, each of the micro piezoelectric elements 19 has an area of 1 $\mu m^2$ or more and not more than 1 $mm^2$, further preferably 100 $\mu m^2$ or more and not more than 10000 $\mu m^2$. Note that the vibrating elements included in the biological measurement apparatus of the present invention may be, e.g., a magnetically-driven element or an electrostatically-driven element, instead of the piezoelectric element exemplified in the present embodiment.

Note that the micro piezoelectric element array 4 may be manufactured by further miniaturizing any conventionally-known two-dimensional piezoelectric element array for use in electronic scanning-type (e.g., phased array-type) ultrasonography by means of the MEMS. Examples of the conventionally-known two-dimensional piezoelectric element array encompass: Kaoru Yamashita, Masanori Okuyama, "*Micro-chouompa array sensor wo mochiita sanjigen keisoku* (Three-dimensional measurement using micro-ultrasonic wave array sensor)", Ultrasonic Wave Techno, Japan Industrial Publishing Co., Ltd., 2005, Vol. 17, No. 2, pages 6 to 12; Kaoru Yamashita, Taisuke Tsurutani, Masanori Okuyama, "*Micro array sensor wo mochiita real-time kuu- chuu chouompa keisokukei* (System for real-time measurement of air-coupled ultrasonic waves using micro array sensor)", The National Convention of the Institute of Electrical Engineering of Japan in 2005 (Tokushima, March 17 to 19), 2005, pages 3 to 156; a micro-ultrasonic array sensor manufactured by Okuyama Laboratory, Graduate School of Engineering Science, Osaka University (http://www.semi.ee.e-s.osaka-u.ac.jp/okuyamalab/study/US.html); and an ultrasonic micro array sensor manufactured by Proassist Ltd. (http://www.tri.pref.osaka.jp/poster/2003/c-45.pdf, http://www.designnewsjapan.com/news/200603/27meas_proassist.html). Further, the conventionally-known two-dimensional piezoelectric element arrays are comprehensively described by Toshikazu Akiyama, Yoshimichi Kitagawa, Kenya Mizoguchi, "*Chouompa sanjigen-hyouji to compound hou* (Three Dimensional Ultrasound & Compound Method)", The Journal of the Japan Society of Radiological Technology, 2004, Vol. 60, No. 5, pages 654 to 660.

The sound sending/receiving unit 3 includes an electromagnetic wave sending/receiving system 8. The electromagnetic wave sending/receiving system 8 includes an electromagnetic wave antenna 9 (electromagnetic wave receiving element, electromagnetic wave emitting element) and an electromagnetic wave sending/receiving circuit 10. The electromagnetic wave sending/receiving circuit 10, which is electrically connected with the electromagnetic wave antenna 9, includes an electromagnetic wave receiving circuit 12 and an electromagnetic wave sending circuit 11. That is, in the present embodiment, the electromagnetic wave receiving element and the electromagnetic wave emitting element, each of which is included in the biological measurement apparatus of the present invention, are realized by the single electromagnetic wave antenna 9. The electromagnetic wave antenna 9 is not limited to any specific type, as long as it is capable of transmission and reception within a frequency band to be used. Examples of the electromagnetic wave antenna 9 include a loop antenna and a micro loop antenna. Note that the electromagnetic wave antenna 9 does not need to have directivity. Instead of the electromagnetic wave antenna 9, a SQUID element can be used. This improves the detection sensitivity of an electromagnetic wave.

In the present embodiment, the electromagnetic wave antenna 9, the electromagnetic wave receiving circuit 12, and the electromagnetic wave sending circuit 11 are built into the sound sending/receiving unit 3. Alternatively, the electromagnetic wave antenna 9, the electromagnetic wave receiving circuit 12, and the electromagnetic wave sending circuit 11 may be provided so as to be independent from the sound sending/receiving unit assembly 2. For example, the electromagnetic wave antenna 9 may be positioned in the mouth cavity of the subject 17. Positioning the electromagnetic wave antenna 9 in the mouse cavity reduces effects of unwanted electromagnetic noises coming from the sound sending/receiving unit assembly 2.

[Principle of Biological Measurement Apparatus]

Next, the following will explain the principle on how a nerve cell is vibrated and an electromagnetic wave generated by the nerve cell thus vibrated is detected in order to measure an electric charge of the nerve cell.

The nervous system of the brain or the like is constituted by a quite large number of nerve cells. For example, the cell body (soma), which is a main part of a nerve cell, has a size of approximately 4 $\mu m$ at minimum, and the cell bodies of respective nerve cells in the cerebral cortex are separated from each other at an average distance of approximately 20 $\mu m$.

A nerve cell is polarized by a difference in ionic concentration between the inside and outside of the cell. Repeated polarization and depolarization of the nerve cell causes movement of an electric charge, thereby leading to generation of an electric current. Electrical activities carried out by a number of individual nerve cells interact with each other. In this manner, information processing is conducted in the living body. That is, the biological measurement apparatus of the present invention detects electrical activities of nerve cells in order to grasp information processing activity in the living body.

Here, if an object that is charged with an electric charge Q is reciprocatingly vibrated at an angular frequency ω, an electromagnetic wave having the same angular frequency ω is emitted due to bremsstrahlung of electromagnetism. Note that if a constant electric current is reciprocatingly oscillated at an angular frequency ω, an oscillating electromagnetic field is generated, which is a magnetic field being generated by the above electric current and being oscillating at the angular frequency ω. This oscillating electromagnetic field is a kind of an electromagnetic wave; therefore, the "electromagnetic wave" herein encompasses an "oscillating electromagnetic field".

Now, if the cell wall of or the whole of a nerve cell that is polarized or depolarized is vibrated by, e.g., a sound wave, an electromagnetic wave is generated, as a result of bremsstrahlung according to the Maxwell's equations, which occurs due to the vibration of the nerve cell and an oscillating current generated by the vibration. A strength and a phase of the electromagnetic wave thus generated are determined depending on the amount and the sign of the electric charge of the nerve cell vibrated. Therefore, by measuring an electromagnetic wave emitted in this way, it is possible to quantitatively grasp an electrical activity of a specific nerve cell.

Figure 4:
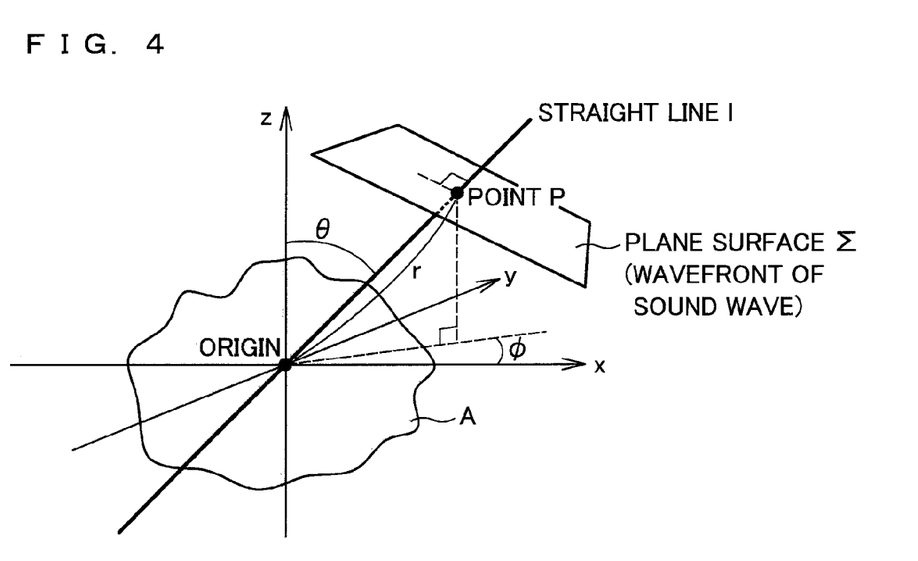
FIG. 4 is a view schematically illustrating the principle of a method for measuring three-dimensional distribution of electrical activities of nerve cells with use of the biological measurement apparatus of the one embodiment of the present invention.
Figure 5:
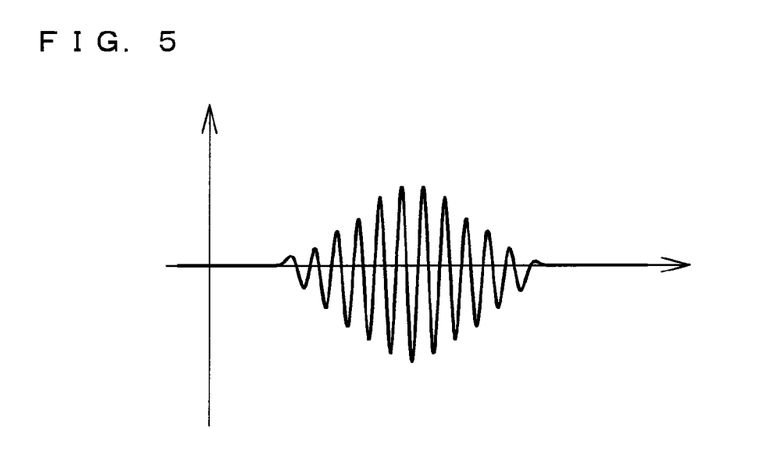
FIG. 5 is a view illustrating an example of a waveform of a sound wave for use in the biological measurement apparatus of the one embodiment of the present invention.

Next, the following will describe, with reference to FIGS. 4 and 5, a method for measuring three-dimensional distribution of electrical activities of nerve cells with use of the biological measurement apparatus 1 of the present embodiment.

FIG. 4 is a view schematically illustrating the principle of the method for measuring three-dimensional distribution of electrical activities of nerve cells with use of the biological measurement apparatus 1 of the present embodiment. FIG. 4 uses (x,y,z) as spatial coordinates for a space in which the subject 17 exists, and shows an example where a pulse sound wave being in the form of a plane wave passes through the subject. In FIG. 4, a straight line 1, which passes through the origin (0,0,0), represents a direction in which the sound wave being in the form of a plane wave propagates, whereas a plane surface Σ, which is always orthogonal to the straight line 1, represents a wavefront observed at a certain time.

FIG. 5 is a view illustrating an example of a waveform of a sound wave used in the biological measurement apparatus 1 of the present embodiment. In FIG. 5, the horizontal axis represents time, whereas the longitudinal axis represents amplitude. For ease of explanation, assume that (i) sizes of respective nerve cells are approximately equal to a wavelength of the sound wave and (ii) a distance between the nerve cells is larger than a pulse width of the sound wave. Further, assume also that an angular frequency of the sound wave is ω.

As shown in FIG. 4, the wavefront of the plane wave represented by the plane surface Σ propagates so as to come close to the origin along the straight line 1 as time advances. Once the wavefront of the plane wave represented by the plane surface Σ reaches the origin, the wavefront propagates inside the subject so as to be far from the origin, without changing its direction.

The straight line 1 can be uniquely identified by a set of angles (θ,ϕ), which is three-dimensional polar coordinates. Further, the plane surface Σ can be uniquely identified by a set (θ,ϕ,r), which includes "r" representing a distance from the origin.

The wavefront propagates inside the subject along the straight line 1 at sonic speed. Therefore, under the approximation that the sonic speed is constant, the distance r can be represented, as a function of time t, as follows: r(t)=constant+t×sonic speed. Thus, a position of the plane surface Σ in terms of time can be represented as (θ,ϕ,r(t)). Note that it is possible to generate a sound wave having such a wavefront by carrying out hologram control or phased-array control in the sound sending/receiving unit assembly 2.

Here, assume that electric charge distribution in the subject at a certain time is ρ(x,y,z). Along with progress of the electrical activity in the subject, the electric charge distribution changes over time at a time scale of approximately 100 Hz. Note that a sound wave propagates through a living body at a speed of approximately 1 km/sec. through approximately 2 km/sec. Thus, 100 Hz is adequately slow, as compared with the time in which a sound wave goes across a biomedical tissue. Thus, ρ(x,y,z) can be regarded as not being changed over time while a sound wave is going across a biomedical tissue.

The sound wave illustrated in FIG. 5 causes nerve cells existing on the wavefront Σ to vibrate uniformly at the angular frequency ω. Note that a speed of an electromagnetic wave is far higher than a sonic speed. Therefore, an electromagnetic wave generated by the nerve cells can be approximated to a combination of electromagnetic waves emitted from the respective points on the wavefront Σ. That is, a waveform of the electromagnetic wave emitted can be represented by the following formula (1), as a function f(θ,ϕ,t) of θ, ϕ, t:

$$f(\theta,\phi,t) = \cos(\omega t) \times \int_{\Sigma(\theta,\phi,r(t))} d\sigma \rho(x,y,z) \tag{1}$$

In the formula (1), the integral is a surface integral on the plane surface Σ specified by (θ,ϕ,r(t)), dσ is a measure of the surface integral of the plane surface Σ, and the argument (x,y,z) of the integrand ρ(x,y,z) represents a position on the plane surface Σ.

That is, in a case where a pulse wave being in the form of a plane wave whose direction is set to (θ,ϕ) is caused to propagate, the electromagnetic wave antenna 9 receives an electromagnetic wave having a waveform represented by f(θϕ,t) in the formula (1). Further, the electromagnetic wave thus received by the electromagnetic wave antenna 9 is homodyne-detected at the angular frequency ω, and is then subjected to a low-pass filter process so that components having frequencies equal to or higher than the angular frequency ω are removed therefrom. Consequently, the following formula (2), which represents amplitude g(θϕ,t) of the frequency f(θϕ,t), is obtained:

$$g(\theta,\phi,t) = \int_{\Sigma(\theta,\phi,r(t))} d\sigma \rho(x,y,z) \tag{2}$$

In actual measurement, measurement is carried out with respect to all directions (θ,ϕ) of the plane wave at a desired angular resolution, and a group of waveforms g(θϕ,t) of respective detected outputs is supplied to a computer. In the formula (2), g(θϕ,t) is converted into ρ(x,y,z) by the three-dimensional Radon transform, which is reversible integrating conversion. Thus, by subjecting g(θϕ,t) to numerical inverse transform by the computer, it is possible to calculate electric charge distribution ρ(x,y,z) in the subject at the time.

Note that carriers having different frequencies may be used, and electromagnetic waves generated may be homodyne-detected with use of the respective carriers. With this, even if a number of plane waves are used at a time, it is possible to measure g(θϕ,t) without causing interference. This makes it possible to significantly reduce time taken for obtaining a group of g(θϕ,t), which is necessary for measurement of ρ(x,y,z).

The foregoing has explained the measurement method that uses (i) a sound wave being in the form of a plane wave and (ii) the three-dimensional Radon transform. This measurement method is suitable for measurement carried out in a wide region of a subject in a short time.

On the other hand, in order to carry out measurement in a narrow region intensively, a pulse sound wave that is converged into the narrow region, e.g., a pulse sound wave being in the form of a spherical pulse or a dipole wave, may be used. For example, (i) a spherical wave that is converged into (X,Y,Z) at a certain time or (ii) a dipole wave that is converged into two points by which (X,Y,Z) is sandwiched and which are far from each other at a distance approximately equal to the wavelength is caused to propagate. Now, assume that the above-described waveform shown in FIG. 5 is used as the waveform of the pulse sound wave. In such a case, at the moment that the pulse sound wave is converged, a region close to the convergent point vibrates at the angular frequency ω, which results in generation of an electromagnetic wave having a waveform approximately represented by the following formula (3):

$$F(t)=\cos(\omega t) \times \rho(X,Y,Z) \quad (3)$$

After reception of the electromagnetic wave, the electromagnetic wave is subjected to the homodyne detection and the low-pass filter process as above. This provides amplitude ρ(X,Y,Z) of the electromagnetic wave received. Namely, by (i) scanning the convergent point (X,Y,Z) of the sound wave in a region which is to be measured and (ii) measuring ρ(X,Y,Z) of respective points in the region, it is possible to obtain electric charge distribution ρ(x,y,z). The electric charge distribution obtained here can also be referred as current distribution, since the electric charge distribution is based on the electric charges resulting from oscillating currents generated by oscillations of electric charges of the respective nerve cells.

Next, the following will explain the principle on how a nerve cell is vibrated and an electromagnetic wave is emitted to the nerve cell in order to stimulate the nerve cell.

In a case where an electric conductor is caused to move at a velocity v in a magnetic field B, a Lorentz force acts on an ion and/or an electron of the electric conductor, so that an electromotive force proportional to B×v is generated in the electric conductor along a direction orthogonal both to (i) a direction of the magnetic field B and (ii) a direction in which the electric conductor proceeds at the velocity v. An electromotive force generated in a case where (i) the magnetic field B is oscillated in simple harmonic motion at a frequency Ω and (ii) the electric conductor is oscillated in simple harmonic motion at a frequency ω is represented by sin((Ω+ω)t)+sin(|Ω−ω|t), in which a sum of frequencies (Ω+ω) and a difference of frequencies |Ω−ω| are combined based on product-sum relationship according to the trigonometrical function. Here, a biomedical tissue such as a nerve cell is an electric conductor, whose carrier is an ion and/or an electron. Therefore, in a case where a nerve cell is vibrated with a sound wave and is irradiated with e.g., an electromagnetic wave so that an oscillating magnetic field is given thereto, an electromotive force is generated in the biomedical tissue. The mechanism of generation of the electromotive force can be expressed as a dynamo provided in a living body, which dynamo is driven by the vibration given by a sound wave.

For example, in a case where the biological measurement apparatus 1 of the present embodiment emits an electromagnetic wave having a frequency Ω to a nerve cell and vibrates the nerve cell by a sound wave having the frequency ω, the nerve cell is oscillated in single harmonic motion at the frequency ω in a magnetic field B which is oscillated in single harmonic motion at the frequency Ω. This results in generation of an electromotive force. Note that the electromotive force caused to be generated in the nerve cell in response to application of the vibration and the electromagnetic wave is herein referred to as an "electrical stimulation".

As described later, the biological measurement apparatus 1 of the present embodiment uses a sound wave and an electromagnetic wave each having a frequency of 1 MHz or greater; therefore, the sum of frequencies (Ω+ω) becomes large. However, such the large frequency results in generation of an electromotive force whose frequency is too high for a nerve cell. Therefore, a vibration component derived from the sum of frequencies (Ω+ω) cannot be an electrical stimulation for a nerve cell. This is based on the principle (the principle of radio-frequency electrocautery) that, even if an alternate current having a high frequency is applied to a nerve cell, the nerve cell cannot respond to it because the frequency is too high, and accordingly the alternate current cannot be an electrical stimulation for the nerve cell.

In a case where the difference of frequencies |Ω−ω| is zero or as low as several hundred Hz, an electrical activity of the biomedical tissue is affected by an electromotive force resulting from a vibration component derived from the difference of frequencies |Ω−ω|. That is, only in a case where a value of the frequency Ω of the electromagnetic wave is close to a value of the frequency ω of the sound wave, an electrical stimulation is given to the biomedical tissue. In particular, in a case where Ω=ω, a direct-current electrical stimulation is given to the biomedical tissue.

For example, assume the case where the sound wave shown in FIG. 5 is used, which sound wave is obtained by modulating a carrier of the angular frequency ω into a pulse-like wave. In such a case, at the moment when a wavefront of the sound wave is converged into a target nerve cell, an electromagnetic wave having the frequency ω, which is the same as that of the sound wave, is emitted to a convergent point. This results in generation of a direct-current electromotive force in the convergent point. This electromotive force becomes as an electrical stimulation for the nerve cell.

[Operation of Biological Measurement Apparatus]

Next, the following will explain how the biological measurement apparatus 1 of the present embodiment operates.

Firstly described is a case where an electric charge of a nerve cell is measured with use of the biological measurement apparatus 1 of the present embodiment.

The micro piezoelectric elements 19 are independently controlled by the computer 13, so that a waveform of a sound wave emitted by each of the micro piezoelectric elements 19 is controlled. The sound wave emitted by each of the micro piezoelectric elements 19 is controlled so as to have a frequency of 1 MHz or more and not more than 1 GHz. Under the control of the computer 13, the piezoelectric element driving circuit array 6 operates so as to cause a corresponding micro piezoelectric element 19 to emit a sound wave.

The sound wave to be emitted by the micro piezoelectric element 19 is preferably a pulse plane wave which has been AM-modulated into a pulse-like wave. Here, the time scale of an electrical activity of a nerve cell is approximately 100 Hz. Therefore, based on this value, the frequency of the sound wave to be emitted by the micro piezoelectric element 19 may be optionally set depending on the desired spatial resolution, etc. Preferably, however, the frequency of the sound wave is 1 MHz or more and not more than 1 GHz. The sound wave having a frequency of 1 MHz or more and not more than 1 GHz has a wavelength approximately equal to a length of a nerve cell; therefore, use of the sound wave having such the frequency improves a spatial resolution for measurement, thereby making it possible to carry out measurement on individual nerve cells favorably.

By causing a number of micro piezoelectric elements 19, which constitute the sound sending/receiving unit assembly 2, to be controlled by the computer 13, it is possible to emit a sound wave having any waveform in any direction within the brain. For example, by carrying out hologram control or phased-array control in the sound sending/receiving unit assembly 2 under the control of the computer 13, it is possible to generate, in a living body, a plane wave, a spherical wave, a dipole wave, or the like, each of which has a desired waveform.

The sound wave emitted by the micro piezoelectric element 19 vibrates a nerve cell in the subject. Since the nerve cell has an electric charge, vibrating the nerve cell results in generation of an electromagnetic wave, as described previously. Then, the electromagnetic wave thus generated is received by the electromagnetic wave antenna 9, and converted into numerical data by the electromagnetic wave receiving circuit 12, which is then supplied to the computer 13. Then, the computer 13 processes the numerical data according to the desired image display method such as a cross-sectional diagram, three-dimensional plotting, three-dimensional contour lines, grayscale display, and/or a moving image. Thereafter, the data thus processed is visualized by the display device 14.

In the case where the pulse plane wave is used as described previously, the sound wave causes one cross-section of the subject, through which the pulse wavefront transmits, to vibrate at a frequency of the sound wave. Then, an electromagnetic wave is generated according to an electric charge of the one cross-section. By measuring electromagnetic waves generated in this manner, it is possible to obtain information indicative of layered electric charge distributions of respective cross-sections. Further, measurement is carried out while changing a direction (traveling direction) of the wavefront of the pulse wave, so as to measure electromagnetic waves generated by cross-sections in various directions. Information thus obtained from the cross-sections may be processed by the computer 13 with use of a mathematical technique such as the three-dimensional inverse Radon transform as described previously. This provides three-dimensional electric charge distribution.

A method for detection of the electromagnetic wave may be homodyne detection as described previously, since the frequency of the sound wave is equal to that of an electromagnetic wave to be generated. Alternatively, an inner product of orthogonal wavelet functions may be used as the detection. In the orthogonal wavelet functions, a waveform may be used as a pulse wave, and the inner product thereof may be obtained by the computer 13 carrying out numerical convolution on waveforms of electromagnetic waves generated. Using, as the detection, the inner product of the orthogonal wavelet functions is efficient, in a case where a number of pulse plane waves are used at once.

In measurement on nerve cells in a broad region, it is preferable to emit a pulse plane wave as described previously and to carry out an analysis by, e.g., the three-dimensional Radon transform.

In measurement on electrical activities of nerve cells in a narrow region, a sound wave that is to be converged into the narrow region, e.g., a sound wave being in the form of a spherical pulse plane wave or a dipole pulse plane wave, may be used as described previously. At the moment when a wavefront of the pulse plane wave is converged, only the convergent point is vibrating. Thus, a detected output of an electromagnetic wave to be detected reflects electrical activities of the nerve cells in the convergent point. By emitting the sound wave so that the sound wave scans the convergent point, it is possible to obtain three-dimensional distribution of the electrical activities in the narrow region. In this process, analysis means such as the spherical Radon transform may be used.

Either with the pulse wave, the spherical wave, or the dipolar wave, it is possible to carry out measurement without causing interference, in such a manner that pulse sound waves having carriers of different frequencies are emitted, and then homodyne detection is carried out so as to separate the pulse sound waves from one another according to their frequencies. Thus, use of a number of pulse waves at once makes it possible to concurrently carry out measurements with the pulse waves. This improves the temporal resolution.

In the biological measurement apparatus 1 of the present embodiment, (i) a sound wave which is emitted by one of the micro piezoelectric elements 19 and is then reflected by the subject 17 or (ii) a sound wave which is emitted by the one micro piezoelectric element 19 and is then transmitted through the subject 17 can be detected by the one micro piezoelectric element 19 or another one of the micro piezoelectric elements 19. Based on the sound wave thus detected, the sound wave detecting circuit array 7 can check if the sound wave has propagated inside the subject accurately. For example, in order to carry out measurement and/or stimulation with respect to the brain noninvasively, it is necessary to accurately emit a plane wave, a spherical wave, or the like into a brain tissue after reducing effects of reflection, refraction, and/or dispersion caused by the cranial bone, which has great acoustic impedance. For this purpose, the sound wave detecting circuit array 7 detects the sound wave reflected by or transmitted through the subject, and also measures distribution of acoustic impedance within the subject, etc. Based on the detection result, it is possible to control the piezoelectric element driving circuit array so as to (i) correct non-uniform distribution of the acoustic impedance and/or the sonic speed or (ii) emit a sound wave which cancels the reflection. Further, by carrying out a numerical analysis while considering the actual non-uniform distribution of the acoustic impedance and/or the sonic speed, it is possible to improve the accuracy of the measurement.

Next, the following will describe a case where an electrical stimulation is given to a nerve cell with use of the biological measurement apparatus 1 of the present embodiment. For ease of explanation, features in common with the above-described measurement of an electric charge of a nerve cell are not explained here.

The electromagnetic wave antenna 9 emits an electromagnetic wave to a region including a target nerve cell to which an electrical stimulation is to be given. Further, the computer 13 controls the piezoelectric element driving circuit array 6 so that the nerve cell is irradiated with a sound wave from a corresponding micro piezoelectric element 19 at least at the moment that the electromagnetic wave transmits through the nerve cell. That is, under the control of the computer 13, the piezoelectric element driving circuit array 6 and the electromagnetic wave sending circuit 11 are operated, and the corresponding micro piezoelectric element 19 and the electromagnetic wave antenna 9 emit a sound wave and an electromagnetic wave, respectively. Since the target nerve cell, which is caused to exist in a magnetic field due to the electromagnetic wave, is vibrated by the sound wave, an electromotive force is generated as described previously. Due to the electromotive force, an electrical stimulation is given to the target nerve cell. Preferably, the electromagnetic wave and the sound wave are set to have an identical frequency. The reason for this is that this causes generation of a direct-current electromotive force in the nerve cell, and the direct-current electromotive force carries a net electric charge, so as to reliably stimulate the cell.

Each of (i) a frequency of the electromagnetic wave emitted by the electromagnetic wave antenna 9 and (ii) a frequency of the sound wave emitted by the micro piezoelectric element 19 is controlled by the computer 13 so as to be 1 MHz or more and not more than 1 GHz. Note that each of the frequency of the sound wave and the frequency of the electromagnetic wave is not limited to 1 MHz or more and not more than 1 GHz. The time scale of an electrical activity of a nerve cell is approximately 100 Hz; therefore, based on this value, each of the frequency of the sound wave and the frequency of the electromagnetic wave may be set depending on the desired spatial resolution, etc. Preferably, however, each of the frequency of the sound wave and the frequency of the electromagnetic wave is 1 MHz or more and not more than 1 GHz. Since the sound wave having a frequency of 1 MHz or more and not more than 1 GHz has a wavelength approximately equal to a length of a nerve cell, such the sound wave can favorably stimulate individual cells. Note that the sound wave emitted by the micro piezoelectric element 19 is not particularly limited, examples of which encompass a spherical wave or a dipole wave each of which is obtained by AM-modulating a carrier into a pulse-like wave.

According to the Fleming's law, a sign and a direction of the electromotive force serving as the electrical stimulation can be controlled by adjusting, e.g., (i) a direction of vibrations of the sound wave, (ii) a direction of vibrations of a magnetic field component of the electromagnetic wave, and/or (iii) phases of the sound wave and the electromagnetic wave. By using sound waves and electromagnetic waves having various frequencies, it is possible to stimulate a number of nerve cells at once without causing interference. Preferably, the biological measurement apparatus of the present invention includes a large number of electromagnetic wave emitting elements. For example, as in the present embodiment, use of the electromagnetic wave antenna 9 enables emission of electromagnetic waves having various frequencies at once with a single antenna, and use of an increased number of electromagnetic wave antennas 9 enhances an intensity of an electromagnetic wave to be emitted per nerve cell.

Thus, use of the biological measurement apparatus 1 of the present embodiment makes it possible to generate an electromotive force in any nerve cell in the subject with a spatial resolution of a nerve cell size. With this, it is possible to interfere and/or interrupt an information processing activity in a living organism, and also to control the interference and/or the interruption.

In other words, the biological measurement apparatus 1 of the present embodiment is an embodiment of the biological stimulation apparatus of the present invention. That is to say, the micro piezoelectric element 19 (vibrating element) vibrates a nerve cell of the subject, and the electromagnetic wave antenna 9 (electromagnetic wave emitting element) emits an electromagnetic wave to the nerve cell, so that an oscillating magnetic field is formed around the nerve cell. This results in generation of an electromotive force in the nerve cell. In this manner, it is possible to give an electrical stimulation to the nerve cell.

According to the biological measurement apparatus 1 of the present embodiment, it is possible to directly provide the brain with information by giving an electrical stimulation to a nerve cell in the brain under the control of the computer 13. In this operation, it is possible to give an electrical stimulation to the nerve cell in such a manner as to feed back a measurement result of an electrical activity of the nerve cell.

That is, in the present embodiment, the measurement result of the electrical activity in the brain is supplied to the external device 20 via the input/output device 15, and the external device 20 is operated according to this.

For example, in a case where a television camera or a microphone is used as the external device 20, information obtained by the television camera or the microphone can be directly transmitted to the brain.

Assume a case where a television camera, serving as the external device 20, is connected to the input/output device 15. In this case, nerve cells in the visual area in the brain of a visually-impaired person (subject 17) may be stimulated by an electromagnetic wave according to video information obtained by the television camera, and the nerve cells may be vibrated so that electric charges of the nerve cells are measured. Then, the result of the measurement may be fed back thereto. In this way, the television camera can be used as an artificial eye. Similarly, by selecting a sensor corresponding to each sensation such as acoustic sense, tactile sense, gustatory sense, or olfactory sense, it is possible to overcome any disorders of sensation. For another example, electrical activities of nerve cells in the motor area in the brain of a person handicapped in the arm and/or leg (subject 17) may be measured, and an actuator integrated in an artificial arm and/or an artificial leg may be controlled according to the result of the measurement. This provides the artificial arm and/or the artificial leg which moves almost like a natural arm and/or leg, according to the intention of the handicapped person (subject 17).

As described above, the present invention enables direct information exchange (interface) between the brain of the subject 17 and the computer 13. Therefore, the present invention can provide a direct interface between the brain of the subject 17 and any type of external device 20 via the computer 13. This makes it possible to provide (i) a machine that a user can operate merely by thinking and (ii) a machine that directly transmits information to one's thought. That is, with this direct interface between the brain and the computer 13, it is possible to directly operate, from the brain of the subject 17, any type of external device 20 such as an automobile, an aircraft, a robot, an industrial machine, or a toy.

Furthermore, with the present embodiment, it is possible to carry out, via the Internet 16, direct communication between brains, expansion of brain function by causing information processing in the brain to be carried out externally, etc.

Thus, by using the biological measurement apparatus 1 of the present embodiment, it is possible to provide a direct interface between the brain and a computer. This direct interface is different from a conventional interface between a human and a computer whish uses a display device and a keyboard. Thus, it is possible to provide a higher-speed, larger-capacity interface. With this, the brain and a computer can carry out information processing (e.g., calculations and/or thinking) in a manner as if the brain and the computer are integrated into one.

Moreover, use of the biological measurement apparatus 1 of the present embodiment enables direct information exchange with the brain of another person or animal.

In addition, the present invention can be applied to treatments to diseases caused by an abnormity in a nerve cell, such as the Parkinson's disease and severe depression. The treatment can be carried out in the following manner: an electrical stimulation is given to a nerve cell which is associated with a disease to be treated, so that a normal nervous system free from symptoms of the Parkinson's disease or the like is constructed. Namely, the computer 13 calculates an electrical stimulation which is to be given to a nerve cell and which is necessary to construct a target nervous system. Based on the calculation result, signals for emitting a sound wave and an electromagnetic wave, each of which is for giving the electrical stimulation, are supplied to a corresponding micro piezoelectric element 19 and the electromagnetic wave antenna 9 via the piezoelectric element driving circuit array 6 and the electromagnetic wave sending circuit 11, respectively. Thus, it is possible to treat an abnormality in the nervous system. Further, based on the result of measurement carried out by the biological measurement apparatus 1, the computer 13 can automatically determine the state of the symptoms. Based on the determination result, it is possible to automatically change (i) the target nerve cell to which the electrical stimulation is to be given and/or (ii) an intensity of the electrical stimulation.

This enables noninvasive treatment for the Parkinson's disease or severe depression, each of which has been conventionally treated by an invasive implanted electrode.

Lastly, the blocks of the computer 13 may be realized by way of hardware or software as executed by a CPU as follows:

The computer 13 includes a CPU (central processing unit) and memory devices (memory media). The CPU (central processing unit) executes instructions in control programs realizing the functions. The memory devices include a ROM (read only memory) which contains programs, a RAM (random access memory) to which the programs are loaded, and a memory containing the programs and various data. The objective of the present invention can also be achieved by mounting to the computer 13 a computer-readable storage medium containing control program code (executable program, intermediate code program, or source program) for the computer 13, which is software realizing the aforementioned functions, in order for the computer (or CPU, MPU, etc.) to retrieve and execute the program code contained in the storage medium.

The storage medium may be, for example, a tape, such as a magnetic tape or a cassette tape; a magnetic disk, such as a Floppy (Registered Trademark) disk or a hard disk, or an optical disk, such as CD-ROM/MO/MD/DVD/CD-R; a card, such as an IC card (memory card) or an optical card; or a semiconductor memory, such as a mask ROM/EPROM/EEPROM/flash ROM.

The computer 13 may be arranged to be connectable to a communications network so that the program code may be delivered over the communications network. The communications network is not limited in any particular manner, and may be, for example, the Internet 16, an intranet, extranet, LAN, ISDN, VAN, CATV communications network, virtual dedicated network (virtual private network), telephone line network, mobile communications network, or satellite communications network. The transfer medium which makes up the communications network is not limited in any particular manner, and may be, for example, wired line, such as IEEE 1394, USB, electric power line, cable TV line, telephone line, or ADSL line; or wireless, such as infrared radiation (IrDA, remote control), Bluetooth (Registered Trademark), 802.11 wireless, HDR, mobile telephone network, satellite line, or terrestrial digital network. The present invention encompasses a computer data signal in which the program code is embodied electronically and which is embedded in a carrier wave.

The present invention is not limited to the description of the embodiments above, but may be altered by a skilled person within the scope of the claims. An embodiment based on a proper combination of technical means disclosed in different embodiments is encompassed in the technical scope of the present invention.

As described above, the biological measurement apparatus of the present invention includes: one or more vibrating elements each for vibrating a nerve cell of a subject without coming in contact with the nerve cell; an electromagnetic wave receiving element for receiving an electromagnetic wave generated by the nerve cell which is vibrated by the vibrating element; and an analyzing means for analyzing an amount and a sign of an electric charge of the nerve cell based on the electromagnetic wave received by the electromagnetic wave receiving element. According to this configuration, the biological measurement apparatus of the present invention can vibrate a nerve cell without coming in contact with the nerve cell. Since the nerve cell has an electric charge, vibrating the nerve cell results in generation of an oscillating current. Due to the oscillating current, an electromagnetic wave is generated according to the Maxwell's equations. Then, the electromagnetic wave thus generated is received and converted into numerical data, which is then analyzed by, e.g., the three-dimensional Radon transform. Thus, it is possible to obtain three-dimensional electric charge distribution in nerve cells in the subject. Further, with this configuration, after the sound wave is emitted, an electromagnetic wave generated in response to the emission is received within a quite short time. Therefore, it is possible to measure the electric charge distribution in the subject in real time.

Thus, the present invention involves an advantage of providing a biological measurement apparatus which allows to grasp three-dimensionally and in real time (i) an electric charge distribution in nerve cells in a subject, consequently (ii) an electrical activity in the subject.

Further, as described above, the biological stimulation apparatus of the present invention includes: one or more vibrating elements each for vibrating a nerve cell of a subject without coming in contact with the nerve cell; and an electromagnetic wave emitting element for emitting an electromagnetic wave to the nerve cell vibrated by the vibrating element. According to this configuration, the biological stimulation apparatus of the present invention can vibrate a nerve cell by a vibrating element, and emit an electromagnetic wave to the nerve cell, so that an oscillating magnetic field is formed around the nerve cell. This results in generation of an electromotive force in the nerve cell, according to the Fleming's law.

Thus, the present invention involves another advantage of providing a biological stimulation apparatus capable of giving electrical stimulations to individual nerve cells noninvasively.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

A biological measurement apparatus of the present invention is applicable to medical science fields and medical service fields relating to diagnoses, treatments, and rehabilitation trainings for the brain, nerves, the mind, the spinal cord, the heart, etc. Particularly, the biological measurement apparatus of the present invention is applicable to diagnoses and researches on various diseases and disorders relating to the brain and nerves. Furthermore, with the biological measurement apparatus of the present invention, it is possible to stimulate the hippocampus, etc. of the brain and measure its reaction to the stimulation, so as to carry out operations such as (i) reading, writing, and/or deletion of memory, (ii) strengthening of learning, and/or (iii) external storage of memory. Thus, the biological measurement apparatus of the present invention is applicable to various fields such as medical uses, educational uses, communication technologies, information processing, and recreation (e.g., games).

The invention claimed is:

1. A biological measurement apparatus comprising:
   one or more vibrating elements each for vibrating a nerve cell of a subject without coming in contact with the nerve cell;
   an electromagnetic wave receiving element for receiving an electromagnetic wave generated by the nerve cell which is vibrated by the one or more vibrating elements; and
   an analyzing means for analyzing an amount and a sign of an electric charge of the nerve cell based on the electromagnetic wave received by the electromagnetic wave receiving element,
   wherein the one or more vibrating elements are each configured to emit a sound wave so as to externally vibrate the nerve cell of the subject noninvasively,
   wherein the one or more vibrating elements are provided on a surface of a substrate, the surface configured to face the subject, the substrate configured to cover at least part of a surface of the subject, and wherein the one or more vibrating elements are configured to vibrate at a frequency of 1 MHz to 1 GHz, and wherein the frequency is equal to a frequency of the electromagnetic wave.

2. The biological measurement apparatus as set forth in claim 1, wherein:
   the one or more vibrating elements each have a region whose area is 1 $\mu m^2$ or more and not more than 1 $mm^2$, from which region the sound wave is emitted.

3. The biological measurement apparatus as set forth in claim 1, further comprising:
   a plurality of vibrating means units each provided with a vibrating element array in which the one or more vibrating elements are arranged two-dimensionally.

4. The biological measurement apparatus as set forth in claim 1, wherein:
   the substrate configured to cover at least part of a surface of a head of the subject.

5. The biological measurement apparatus as set forth in claim 1, further comprising:
   an electromagnetic wave emitting element for emitting an electromagnetic wave to the nerve cell.

6. The biological measurement apparatus as set forth in claim 5, wherein:
   at least one of the electromagnetic wave receiving element and the electromagnetic wave emitting element is provided in a vibrating means unit provided with a vibrating element array in which the one or more vibrating elements are arranged two-dimensionally.

7. The biological measurement apparatus as set forth in claim 5, wherein:
   the electromagnetic wave receiving element and the electromagnetic wave emitting element are provided as a single antenna.

8. The biological measurement apparatus as set forth in claim 5, wherein:
   the analyzing means is configured to calculate (i) a requirement for an electrical stimulation to cause a nervous system having an abnormality to be normal and (ii) a requirement for a vibration and an electromagnetic wave to give the electrical stimulation to a nerve cell; and
   based on the requirement for the vibration and the electromagnetic wave, the analyzing means is configured to calculate a signal for driving the one or more vibrating elements and supply the signal to the one or more vibrating elements, and the analyzing means is configured to calculate a signal for driving the electromagnetic wave emitting element and supply the signal to the electromagnetic wave emitting element.

9. The biological measurement apparatus as set forth in claim 1, wherein:
   the analyzing means is configured to analyze a nervous system of the subject based on the electromagnetic wave received by the electromagnetic wave receiving element.

* * * * *